US006495691B1

(12) United States Patent
Horne et al.

(10) Patent No.: US 6,495,691 B1
(45) Date of Patent: Dec. 17, 2002

(54) PROCESS FOR THE PREPARATION OF TETRAHYDROTHIENO[3,2-C]PYRIDINE DERIVATIVES

(75) Inventors: Stephen E. Horne, Burlington (CA); Gamini Weeratunga, Brantford (CA); Bogdan M. Comanita, London (CA); Jaipal Reddy Nagireddy, Brantford (CA); Laura Kaye McConachie, St. George (CA)

(73) Assignee: Brantford Chemicals Inc., Brantford (CA)

( * ) Notice: Subject to any disclaimer, the term of this patent is extended or adjusted under 35 U.S.C. 154(b) by 0 days.

(21) Appl. No.: 09/902,165

(22) Filed: Jul. 11, 2001

(51) Int. Cl.[7] .................... C07D 491/02; C07D 263/02; C07D 333/22
(52) U.S. Cl. .......................... 546/114; 548/215; 549/77
(58) Field of Search ........................ 549/77; 548/215; 546/114

(56) References Cited

U.S. PATENT DOCUMENTS

| 4,051,141 A | 9/1977 | Castaigne | 260/294.8 |
|---|---|---|---|
| 4,127,580 A | 11/1978 | Braye | 546/114 |
| 4,529,596 A | 7/1985 | Aubert et al. | 514/231 |
| 4,847,265 A | 7/1989 | Badorc et al. | 514/301 |
| 5,132,435 A | 7/1992 | Bousquet et al. | 549/60 |
| 5,204,469 A | 4/1993 | Descamps et al. | 546/114 |

FOREIGN PATENT DOCUMENTS

| FR | 2424278 | 11/1979 | ..................... 495/4 |
|---|---|---|---|
| JP | 62-164683 | of 1987 | |
| WO | WO98/39322 | 9/1998 | |
| WO | WO98/51681 | 11/1998 | |
| WO | WO98/51682 | 11/1998 | |
| WO | WO98/51689 | 11/1998 | |
| WO | WO99/18110 | 4/1999 | |

OTHER PUBLICATIONS

J. P. Maffrand, R. Boigegrain, Heterocycles, 1979, 12, 1479.
J. Heterocyclic Chem., 1876, 13, 1347.
Bull. Chem. Soc. Jpn., 1987, 60, 1159.
J. Am. Chem. Soc. 1999, 121, 4284.

*Primary Examiner*—Alan L. Rotman
*Assistant Examiner*—Raymond Covington
(74) *Attorney, Agent, or Firm*—Ivor M. Hughes; Marcelo K. Sarkis; Neil H. Hughes

(57) ABSTRACT

A process for the preparation of tetrahydrothieno[3,2-c] pyridine derivatives of general formula I:

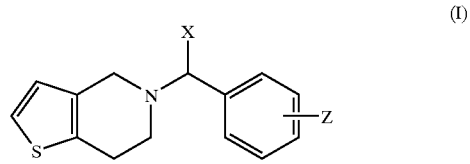

or their pharmaceutically acceptable salts, wherein the meaning of X is hydrogen, carboxyl, alkoxycarbonyl, aryloxycarbonyl, nitrile, or carbamoyl of formula

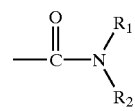

wherein $R_1$ and $R_2$ can be individually or simultaneously hydrogen, alkyl or part of a heterocyclic structure; Z can be hydrogen, halogen, alkyl, aryl, aryloxy or alkoxy group.

28 Claims, No Drawings

PROCESS FOR THE PREPARATION OF TETRAHYDROTHIENO[3,2-C]PYRIDINE DERIVATIVES

FIELD OF INVENTION

The present invention refers to a new process for the synthesis of tetrahydrothieno[3,2-c]pyridine derivatives, in particular 5-o-chlorobenzyl-4,5,6,7-tetrahydothieno[3,2-c]pyridine and racemic or enantiomerically enriched methyl α-(4,5,6,7-tetrahydro-5-thieno[3,2-c]pyridyl)-o-chlorophenylacetate, and intermediates thereof.

BACKGROUND OF THE INVENTION

Structure 1, known as Ticlopidine, is an antithrombotic drug with platelet aggregation inhibiting properties as disclosed in U.S. Pat. No. 4,051,141 and U.S. Pat. No. 4,127,580.

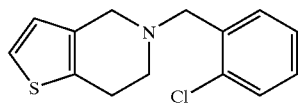

The dextrorotatory enantiomer (Structure 2), bearing the International Non-Proprietary name (INN) Clopidogrel, has the absolute configuration S and is a commercially significant drug with excellent antithrombotic and platelet aggregation inhibiting activity as disclosed in U.S. Pat. No. 4,847,265.

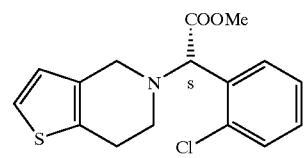

Similar properties are displayed by the less potent racemic mixture (U.S. Pat. No. 4,529,596).

The enantiomerically enriched compound can be prepared by means of enantioselective synthesis or starting from a racemic mixture of enantiomers in conjunction with a resolution process.

A known process for the preparation of racemic Clopidogrel 2 is based on the nucleophilic displacement of racemic α-halophenylacetic acid derivatives 3 by 4,5,6,7-tetrahydrothieno[3,2c]pyridine 4 as described in U.S. Pat. No. 4,529,596 and U.S. Pat. No. 5,132,435 (Scheme 1).

Scheme 1

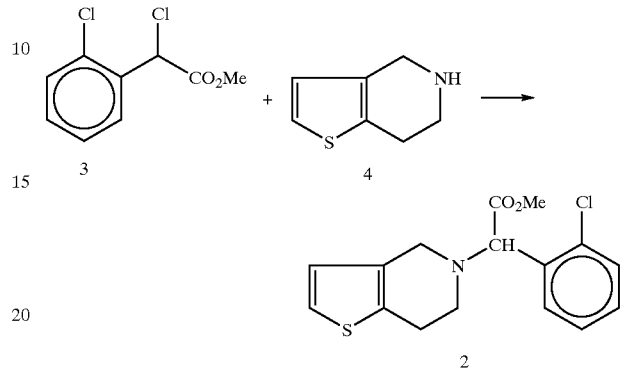

The enantiomerically enriched clopidogrel is obtained through the resolution of the racemic mixture of methyl α-(4,5,6,7-tetrahydro-5-thieno[3,2-c]pyridyl)-o-chlorophenylacetate 2 with R-camphorsulfonic acid as described in U.S. Pat. No. 4,847,265 and U.S. Pat. No. 5,132,435.

Racemic clopidogrel can also be prepared starting with the Strecker synthesis of α-(2-thienyl)ethylamino-o-chlorophenylacetonitrile 6 as shown in Scheme 2. Hydrolysis of the nitrile followed by esterification leads to methyl α-(2-thienyl)ethylamino-o-chlorophenylacetate 8. This in turn generates the tetrahydrothieno[3,2-c]pyridine bicyclic system by reacting with a formylating agent (e.g. paraformaldehyde) under acidic conditions. The process is disclosed in WO 98/51682, WO 98/51689 and WO 98/51681.

Scheme 2

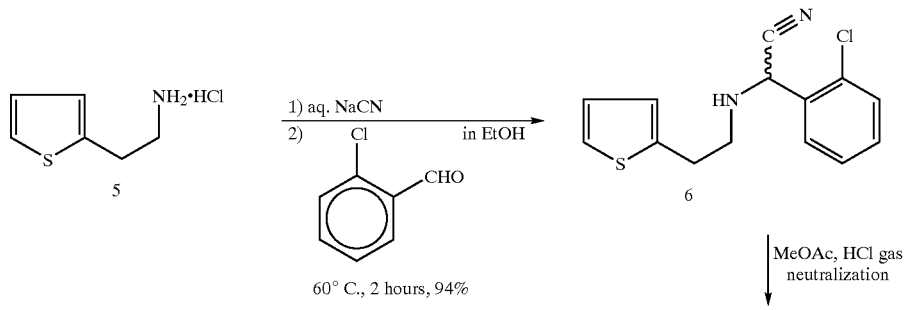

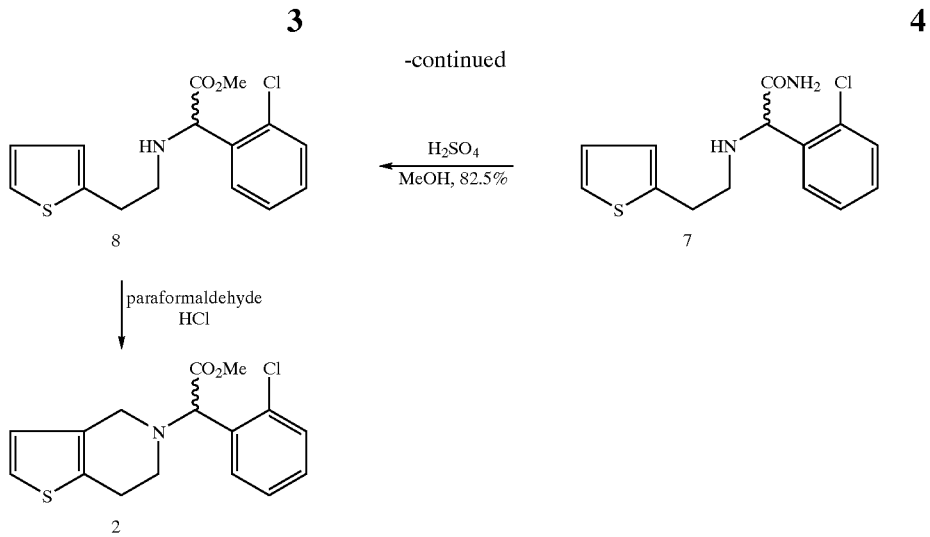

According to these patents (WO 98/51682 WO 98/51689, WO 98/51681), the same reaction scheme can be applied to the preparation of dextrorotatory clopidogrel in combination with the resolution, one of the intermediates. Thus, α-(2-thienyl)ethylamino-o-chlorophenylacetonitrile 6, α-(2-thienyl)ethylamino-o-chlorophenylacetamide 7 and methyl α-(2-thienyl)ethylamino-o-chlorophenylacetate 8 are resolved with enantiomerically enriched camphorsulfonic acid, tartaric acid and camphorsulfonic acid respectively. Each of these enantiomerically enriched intermediates can be transformed stereospecifically to dextrorotatory clopidogrel without significant racemization. Notably, the stereospecificity of the last step in Scheme 2 is also disclosed in U.S. Pat. No. 5,204,469.

An alternative process for the preparation of the dextrorotatory clopidogrel starts with enantiomerically enriched methyl o-chlorophenylglycine 10 and alkali 2-thienylglycidate 9 in the presence of a borohydride reducing agent as reported in WO 98/39322 (Scheme 3).

tetrahydrothieno[3,2c]pyridine 4 as disclosed in WO 99/18110. The same publication documents the reaction of the methyl (R)-α-tosyloxy-o-chlorophenylacetate 11 with 2-(2-thienyl)ethylamine 12 to result in methyl (S)-α-(2-(2-thienyl)ethylamino-o-chlorophenylacetate 8. This in turn generates enantiomerically enriched clopidogrel by reaction with a formylating reagent under acidic conditions. (Scheme 4).

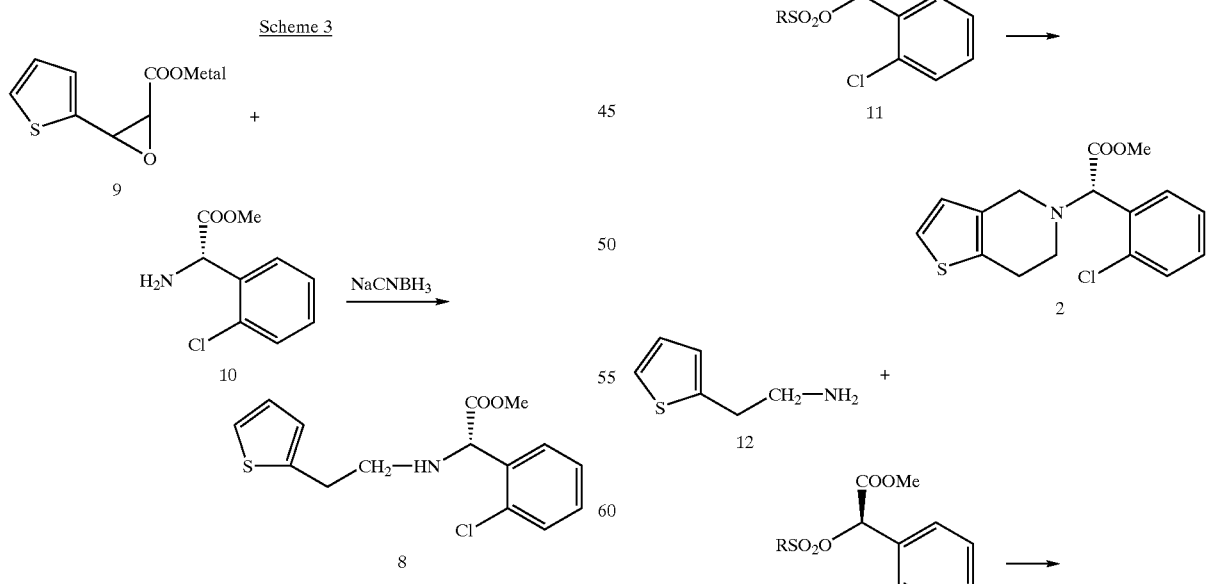

In a different approach, dextrorotatory clopidogrel can be obtained starting from enantiomerically enriched (R)-sulphonyloxyacetic ester derivatives 11 and 4,5,6,7-

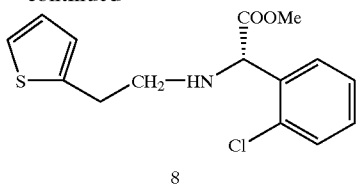

Literature precedent for ticlopidine (J. P. Maffrand, R. Boigegrain, Heterocycles, 1979, 12, 1479; FR 2,424,278) shows that (2-thienyl)ethylene oxide 14 reacts with o-chlorobenzylamine to provide the desired N-(2-(2-thienyl)-2-hydroxyethyl)-o-chlorobenzylamine in low yield due to lack of regioselectivity in the epoxide ring opening (Scheme 5).

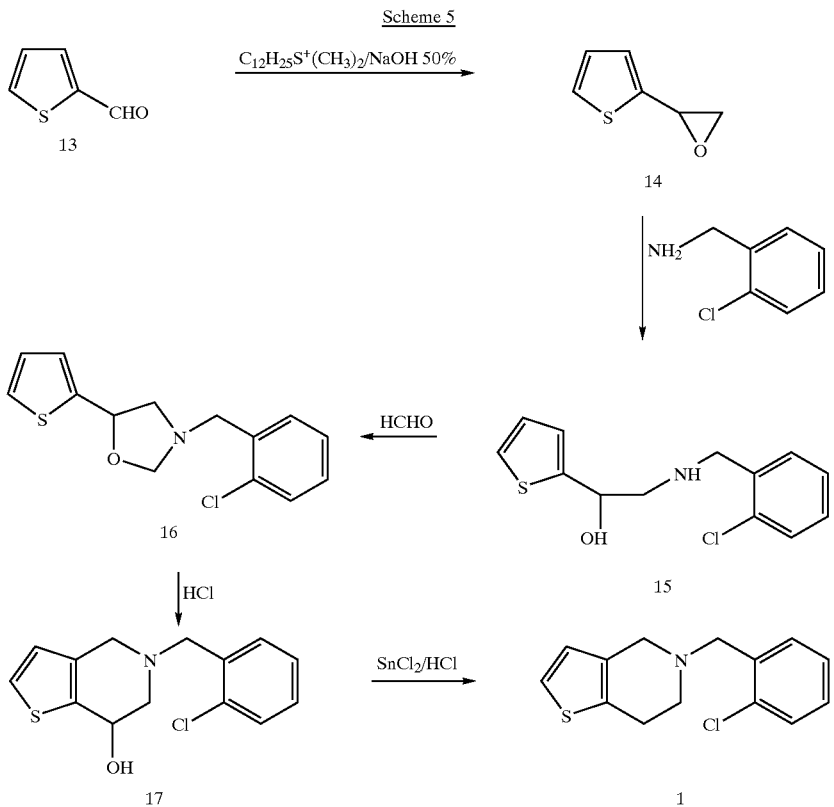

Experiment has shown that further complication arise from the limited stability of the (2-thienyl)ethylene oxide under vacuum distillation and ambient temperature storage conditions. As expected, the extension of this approach to the synthesis of clopidogrel was bridled by lower chemical yield and lack of regioselectivity in the epoxide ring opening step. Moreover, the subsequent thermal rearrangement step leading to the 4,5,6,7-tetrahydrothieno[3,2-c]pyridine skeleton (J. Heterocyclic Chem., 1976, 13, 1347) failed to provide the target hydroxyclopidogrel intermediate under the reported conditions. In conclusion, the use of the (2-thienyl)ethyleneoxide as an intermediate is technically unfeasible while the rearrangement step is substrate dependent and suffers from lack of generality.

It is therefore an object of the present invention to provide an improved process for the preparation of tetrahydrothieno [3,2-c]pyridine derivatives, in particular 5-(2-chlorobenzyl)-4,5,6,7-tetrahydothieno[3,2-c]pyridine and racemic or enantiomerically enriched methyl α-(4,5,6,7-tetrahydro-5-thieno [3,2-c]pyridyl-o-chlorophenylacetate with inexpensive reagents and in good yields.

It is also an object of the present invention to identify novel intermediates which are useful in the manufacture of the above said compounds.

Further and other objects of the invention will be realised from the summary of invention and examples illustrating the invention.

SUMMARY OF THE INVENTION

The present invention provides an improved process for the preparation of a racemic and enantiomerically enriched 4,5,6,7-tetrahydrothieno[3,2-c]pyridines of general formula I

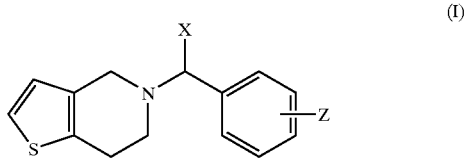

The compound of the general formula I is prepared (Scheme 6) by reducing the compound of formula II with suitable reducing agents, known to those skilled in the art, to a mixture of diastereoisomeric compounds of formula III which are reacted with formaldehyde or any chemical equivalent thereof to yield the compound of formula IV. The compound of formula IV is further rearranged in a suitable solution to produce the compound of formula V which upon reduction (by a suitable reducing agent) provides an enantiomerically enriched or racemic mixture of tetrahydrothieno[3,2-c]pyridine of formula I.

Scheme 6

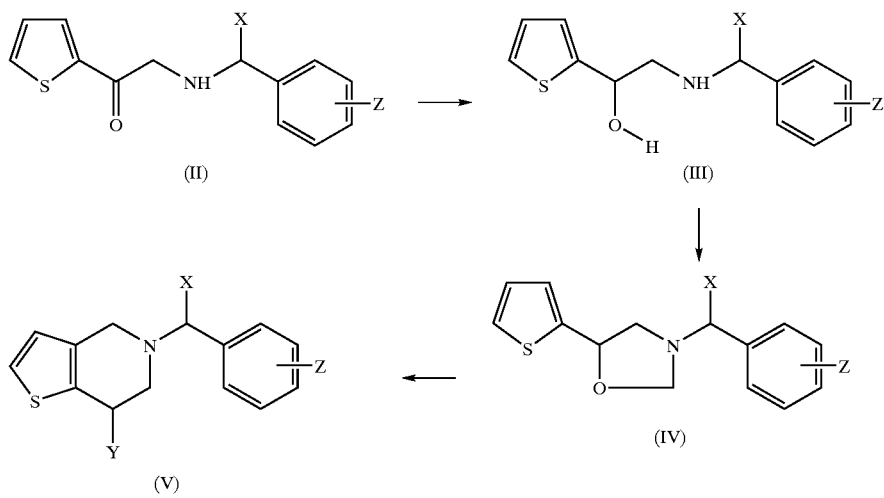

In the general formulae I and V, X can be hydrogen, carboxyl, alkoxycarbonyl, aryloxycarbonyl, nitrile or carbamoyl of formula

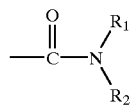

wherein $R_1$ and $R_2$ can be individually or simultaneously hydrogen, alkyl or part of a heterocyclic structure; Y can be hydroxyl, alkanoyloxy, aroyloxy, as well as carbonate derivatives of formula —$OCOOR_3$ or carbamate derivatives of formula —$OCONR_4R_5$ wherein $R_3$ can be substituted or unsubstituted alkyl or aryl; $R_4$ and $R_5$ can be individually or simultaneously substituted or unsubstituted alkyl, aryl or cycloalkyl; Z can be hydrogen, halogen, alkyl, aryl, aryloxy or alkoxy group.

The compound of formula II in its racemic or enantiomerically enriched form is obtained through the reaction of a racemic or enantiomerically enriched primary amine of general formula

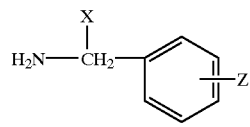

with an α substituted 2-acetylthiophene derivative of general formula

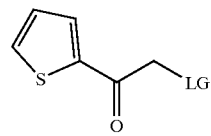

where X and Z have the same meaning as above and LG is a leaving group such as halogen, arysulphonyloxy, aryloxy, sulphonate, alkyloxy and its derivatives or activated aryl. Other obvious synthetic chemical equivalents of the phenylglycine counterpart, such as various salts as well as aliphatic or aromatic esters, amides, nitrile or free carboxyl group are also included in the present invention. The reaction may be carried out in an aromatic solvent (e.g. toluene and the like), polar aprotic solvents (e.g. dimethylformamide, hexamethylphosphoramide, ketones such as acetone, MEK, MIBK and the like), polar protic solvents (e.g. methanol, ethanol, propanol, butanol, n-butanol, isobutanol, n-procanol isopropanol, and the like) or conceivable mixtures thereof.

The process according to one aspect of the present invention improves the previously reported synthesis of ticlopidine and extends the scope of the synthetic sequence to the structurally related clopidogrel.

The process according to a further aspect of the invention circumvents prior art drawbacks and is exemplified by (but not limited to) the specific reaction sequence displayed in Scheme 7.

The starting materials, 2-bromoacetylthiophene 18 and methyl o-chlorophenylglycinate 19 can be prepared according to known literature procedures as reported in Bull. Chem. Soc. Jpn. 60, 1159 and J. Am. Chem. Soc. 1999, 121, 4284 respectively. Racemic or enantiomerically enriched methyl 2-o-chlorophenylglycine 19 reacts with 2-bromoacetylthiophene 18 in the Presence of a base which acts as an acid scavenger.

Scheme 7

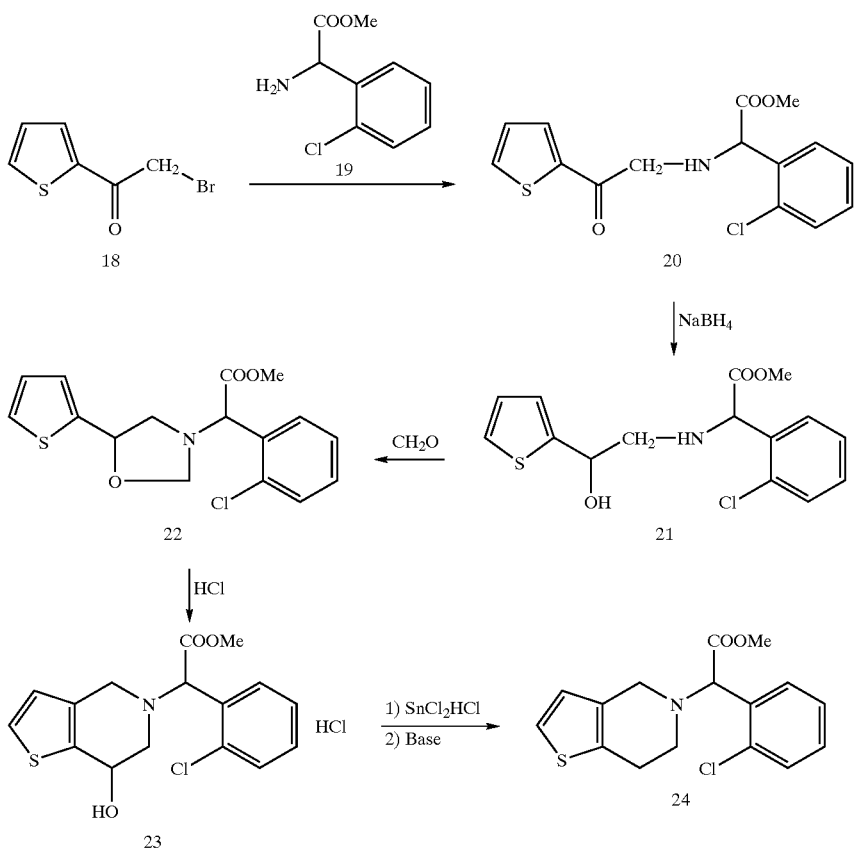

The reduction of the methyl N-(2-(2-thienyl)-2-oxoethyl)-o-chlorophenylglycinate 20 to the corresponding alcohol results in a mixture of diastereoisomeric alcohols methyl N-(2-(2-thienyl)-2-hydroxyethyl)-o-chlorophenylglycinate 21. Reaction with formaline provides the 5-(2-thienyl)-3-(methoxycarbonyl-o-chlorobenzyl)-1,3-oxazolidine 22. Rearrangement of the 5-(2-thienyl)oxazolidine 22 derivative occurs in dry HCl/DMF solution to produce the desired methyl α-(7-hydroxy-4,5,6,7-tetrahydro-5-thieno[3,2-c] pyridyl)-o-chlorophenylglycinate 23. Finally, the alcohol is reduced to the racemic 24 or dextrorotatory clopidogrel 2 by direct dehydroxylation, e.g. treatment with stannous chloride under acidic conditions. Alternatively, derivatization of hydroxyl group to a leaving group followed by reduction or stepwise elimination/reduction of the corresponding 4,5-dihydropyridyl intermediate is conducive to the synthesis of racemic 24 or dextrorotatory clopidogrel 2. Treatment with carbonyl diimidazole, heating, followed by sodium borohydride reduction is provided as a non-limiting example.

The use of o-chlorobenzylamine instead of the methyl glycinate 19 in Scheme 7 provides the process for the synthesis of Ticlopidine.

According to a further aspect of the invention, there are provided novel compounds of formulae 22, 21 and 20 which can be made as a racemic or diasteromeric mixture with set configuration at the carbon adjacent to the nitrogen, as well as its enantiomers either as free base or its salts with Brönstead and Lewis acids. Specific compounds arising from the preparation of formulae 22, 21 and 20 include:

5R-(2-thienyl)-3-(1R-methoxycarbonyl-o-chlorobenzyl)-1,3-oxazoline 5R-(2-thienyl)-3-(1S-methoxycarbonyl-o-chlorobenzyl)-1,3-oxazoline 5S-(2-thienyl)-3-(1R-methoxycarbonyl-o-chlorobenzyl)-1,3-oxazoline 5S-(2-thienyl)-3-(1S-methoxycarbonyl-o-chlorobenzyl)-1,3-oxazoline Methyl N-(2R-(2-thienyl)-2-hydroxyethyl)-2R-o-chlorophenylglycinate Methyl N-(2R-(2-thienyl)-2-hydroxyethyl)-2S-o-chlorophenylglycinate Methyl N-(2S-(2-thienyl)-2-hydroxyethyl)-2R-o-chlorophenylglycinate Methyl N-(2S-(2-thienyl)-2-hydroxyethyl)-2S-o-chlorophenylglycinate Methyl N-(2-(2-thienyl)-2-oxoethyl)-2R-o-chlorophenylglycinate Methyl N-(2-(2-thienyl)-2-oxoethyl)-2S-o-chlorophenylglycinate Further details of the invention are illustrated by reference to the following non-limiting examples:

EXAMPLE 1

(±) Methyl N-2-(2-thienyl)-2-oxoethyl-o-chlorophenylglycinate (20)

2-Bromoacetylthiophene (2.6 g, 12.6 mmol) and methyl o-chlorophenylglycinate (1.94 g, 9.7 mmol) was dissolved in toluene and DMF was added to the reaction mixture. This was treated with potassium carbonate (2 g, 14.6 mmol) and the content was stirred at 60° C. When no more starting aminoester is present, the reaction is stopped and filtered. The cake is washed with toluene and the filtrate extracted with aqueous HCl. The aqueous phase was extracted once more with toluene, brought to pH=8 and back extracted with toluene. The organic solution was evaporated to provide 1.65 g of racemic product. $^1$H-NMR (CDCl3, ppm) 7.65 (2H, dd), 7.45 (1H, m), 7.38 (1H, m), 7.2–7.3 (2H, m), 7.05 (2H, dd), 5.05 (1H, s), 4.05 (2H, dd), 3.72 (3H, s), 3.0 (1H, bs).

EXAMPLE 2

(±) Methyl N-(2-(2-thienyl)-2-hydoxyethyl)-2-o-chlorophenylglycinate (21)

Methyl N-2-(2-thienyl)-2-oxoethyl)-o-chlorophenylglycinate (20) (5.4 g, 16.6 mmol) was dissolved in methanol and treated with sodium borohydride (0.69 g, 18.3 mmol). The reaction is allowed to stir at room temperature over the night and treated with 2N hydrochloric acid to acidic pH. Most of the methanol is evaporated under vacuum and then the remaining aqueous solution partitioned between methylene chloride and 5% sodium hydroxide. The basic aqueous phase is extracted once more with methylene chloride and the combined organic solution is dried on sodium sulfate and evaporated under vacuum to yield 5.2 g of the desired product as a mixture of diastereoisomers. $^1$H-NMR (CDCl3, ppm) 7.4 (1H, m), 7.25 (4H, m), 6.95 (2H, m), 4.9–5.05 (2H, m), 3.75 (3H, s), 2.6–3.1 (2H, m).

EXAMPLE 3

(±) 5-(2-thienyl)-3-(methoxycarbonyl-o-chlorobenzyl)-1,3-oxazoline (22)

Methyl N-(2-(2-thienyl)-2-hydoxyethyl)-2-o-chlorophenylglycinate (21) (2.5 g, 7.6 mmol) was dissolved in ethanol and treated with 37% formaline (1.85 g, 22.8 mmol), then heated at 40° C. over the night under nitrogen. The ethanol is evaporated under vacuum and the residual water was removed by azeotropic distillation with toluene to provide 2.3 g of desired product as a mixture of diastereoisomers. $^1$H-NMR (CDCl3, ppm) 7.72 (1H, m), 7.43 (1H, m), 7.2–7.3 (2H, m), 7.15 (1H, m), 6.95 (2H, m), 5.35 (1H, q), 5.15 and 5.05 (2H, 2s), 4.55 (2H, q), 4.40 (2H, q), 3.75 and 3.70 (3H, 2s), 3.3–3.5 (1H, m), 2.9–3.1 (1H, m).

EXAMPLE 4

(±) Methyl α-(7-Hydroxy-4,5,6,7-tetrahydro-5-thieno[3,2-c]pyridyl)-o-chlorophenylacetate (23)

5-(2-thienyl)-3-(methoxycarbonyl-o-chlorobenzyl)-1,3-oxazoline (22) (5 g, 14.7 mmol) was dissolved in 5 mL of dry DMF and the solution was added dropwise at 0–5° C. over HCl in dry DMF. The reaction was subsequently allowed to warm to room temperature and stirred to complete transformation of the starting material. The solution was partitioned between 1 M sodium bicarbonate solution and toluene. The organic phase was dried on sodium sulfate filtered through a plug of silica gel and evaporated under vacuum to yield 4.3 g of product. $^1$H-NMR (CDCl3, ppm) 7.45–7.55 (1H, m), 7.35–7.45 (1H, m), 7.2–7.35 (2H, m), 7.2 (1H, d), 6.68 (1H, dd), 5.09 and 5.03 (1H, 2 s), 4.68 (1H, bs), 3.5–4.0 (5H, m), 2.7–3.2 (3H, m).

EXAMPLE 5

(±) Methyl α-(4,5,6,7-tetrahydro-5-thieno[3,2-c]pyridyl)-o-chlorophenylacetate (24)

(±) Methyl α-(7-hydroxy-4,5,6,7-tetrahydro-5-thieno[3, 2-c]pyridyl)-o-chlorophenylacetate (23) (0.21 g, 0.622 mmol) was dissolved in acetic acid (4 mL) and treated sequentially with conc. HCl and SnCl$_2$ dihydrate (0.28 g, 1.243 mmol). The reaction was allowed to stir overnight and the solvent was evaporated under vacuum. The residue was partitioned between ethyl acetate and saturated sodium bicarbonate and the ethyl acetate layer was concentrated to provide clopidogrel free base as an oily product (0.16 g). $^1$H-NMR (CDCl3, ppm) 7.7 (1H, dd), 7.35 (1H, m), 7.2–7.35 (2H, m), 7.2 (1H, d), 6.68 (1H, dd), 4.95 (1H, s), 4.68 (1H, bs), 3.5–4.0 (2H, m), 3.75 (3H, s), 2.9 (4 H, s).

EXAMPLE 6

Methyl N-(2-(2-thienyl)-2-oxoethyl)-2S-o-chlorophenylglycinate (20)

Methyl(S)-o-chlorophenylglycinate (6.5 g, 0.032 mol) was dissolved in toluene and treated with potassium carbonate (6.62 g, 0.048 mol) and 2-bromoacetylthiophene (7.2 g 0.035) mol. DMF was added to the reaction mixture and the content was stirred under nitrogen at room temperature. When the whole quantity of aminoester is consumed, the reaction mixture is partitioned between toluene and water and the aqueous layer back extracted several times with toluene. The combined organic phase is extracted with brine, then with 2 N HCl. The aqueous phase was treated with sodium bicarbonate solution to basic pH and extracted with toluene. After the concentration of the toluene solution one obtains 7.3 of oily product that solidifies upon cooling to 0° C. $^1$H-NMR (CDCl3, ppm) 7.65 (2H, dd), 7.45 (1H, m), 7.38 (1H, m), 7.2–7.3 (2H, m), 7.05 (2H, dd), 5.05 (1H, s), 4.05 (2H, dd), 3.72 (3H, s), 3.0 (1H, bs); chiral HPLC 95:5 enantiomeric ratio.

EXAMPLE 7

Methyl N-(2-(2-thienyl)-2-hydoxyethyl)-2S-o-chlorophenylglycinate (21)

Methyl N-(2-(2-thienyl)-2-oxoethyl)-2S-o-chlorophenylglycinate (20) (6.2 g, 19 mmol) was dissolved in methanol and treated in portions with sodium borohydride (0.79 g, 21 mmol) to keep the temperature below 10° C. The reaction is allowed to stir at room temperature for two hours and treated with 2N hydrochloric acid to acidic pH. Most of the methanol is evaporated under vacuum and then the remaining aqueous solution partitioned between methylene chloride and aqueous sodium bicarbonate. The organic solution is dried on sodium sulfate, filtered through a 10% w/w silica gel plug and then evaporated under vacuum to yield 5.9 g of the desired product as a mixture of diastereoisomers. $^1$H-NMR (CDCl3, ppm) 7.4 (1H, m), 7.25 (4H, m), 6.95 (2H, m), 4.9–5.05 (2H, m), 3.75 (3H, s), 2.6–3.1 (2H, m).

EXAMPLE 8

5-(2-thienyl)-3-(1S-methoxycarbonyl-o-chlorobenzyl)-1,3-oxazoline (22)

Methyl N-(2-(2-thienyl)-2-hydoxyethyl)-2S-o-chlorophenylglycinate (21) (5.5 g, 16.8 mmol) was dissolved in ethanol and treated with 37% formaline (4.08 g, 50.4 mmol), then heated at 40° C. under nitrogen. After four hours, the ethanol is evaporated under vacuum and the residual water was removed by azeotropic distillation with toluene to provide 5.6 g of desired product as a mixture of diastereoisomers. $^1$H-NMR (CDCl3, ppm) 7.72 (1H, m), 7.43 (1H, m), 7.2–7.3 (2H, m), 7.15 (1H, m), 6.95 (2H, m), 5.35 (H, q), 5.15 and 5.05 (1H,2 s), 4.55 (2H, q), 4.40 (2H, q), 3.75 and 3.70 (3H, 2 s), 3.3–3.5 (1H, m), 2.9–3.1 (1H, m).

EXAMPLE 9

Methyl(S)-α-(7-hydroxy-4,5,6,7-tetrahydro-5-thieno[3,2-c]pyridyl)-o-chlorophenylacetate (23)

5-(2-thienyl)-3-(1S-methoxycarbonyl-o-chlorobenzyl)-1,3-oxazoline (22) (5.5 g, 16.8 mmol) was dissolved in 5 mL of dry DMF and the solution was added dropwise at 0–5° C. over HCl in dry DMF. The reaction was subsequently allowed to warm to room temperature and stirred over the night at 35° C. to completion. The solution was cooled to room temperature and partitioned between 1 M sodium bicarbonate solution and ethyl acetate. The aqueous phase is back extracted twice with ethyl acetate. The combined organic phase was dried on sodium sulfate filtered and evaporated under vacuum to yield 5.7 g of product as a mixture of two diastereoisomers. $^1$H-NMR (CDCl3, ppm) 7.45–7.55 (1H, m), 7.35–7.45 (1H, m), 7.2–7.35 (2H, m), 7.2 (1H, d), 6.68 (1H, dd), 5.09 and 5.03 (1H, 2 s ), 4.68 (1H, bs), 3.5–4.0 (5H, m), 2.7–3.2 (3 H, m).

EXAMPLE 10

Methyl(S)-α-(4,5,6,7-tetrahydro-5-thieno[3,2-c]pyridyl)-o-chlorophenylacetate (2)

Methyl(S)-α-(7-hydroxy-4,5,6,7-tetrahydro-5-thieno[3,2-c]pyridyl)-o-chlorophenylacetate (1 g, 2.95 mmol) was dissolved in acetic acid (18.8 mL) and treated sequentially with conc. HCl and SnCl$_2$ dihydrate (1.4 g, 6.2 mmol). The reaction was allowed to stir under nitrogen and the solvent was evaporated under vacuum after its completion. The residue was basified with aqueous sodium bicarbonate and extracted repeatedly with ethyl acetate. The combined organic layer was dried, filtered and concentrated to provide clopidogrel free base as an oily product (0.75 g). $^1$H-NMR (CDCl3, ppm) 7.7 (1H, dd), 7.35 (1H, m), 7.2–7–35 (2H, m), 7.2 (1H, d), 6.68 (1H, dd), 4.95 (1H, s), 4.68 (1H, bs), 3.5–4.0 (2H, m), 3.75 (3H, s), 2.9 (4H, s); chiral HPLC 98:2 enantiomeric ratio.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for the preparation of tetrahydrothieno[3,2-c]pyridine derivatives of general formula I:

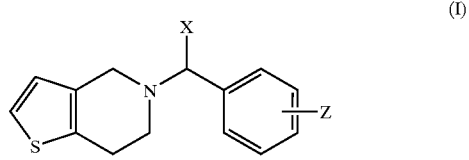

(I)

or their pharmaceutically acceptable salts, wherein the meaning of X is carboxyl, alkoxycarbonyl, aryloxycarbonyl, or carbamoyl of formula

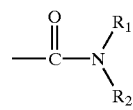

wherein R$_1$ and R$_2$ can be individually or simultaneously hydrogen, alkyl or part of a heterocyclic structure; Z can be hydrogen, halogen, alkyl, aryl, aryloxy or alkoxy group comprising the steps of:

(a) reducing the compound of formula II with suitable reducing agents to obtain compound of formula III,

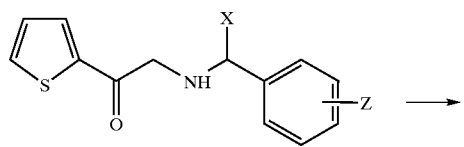

(II)

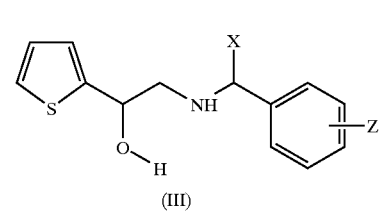

(III)

(b) reacting the compound of formula III with formaldehyde or any chemical equivalent thereof to obtain compound of formula IV,

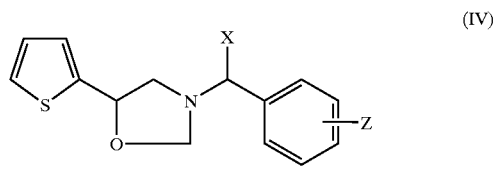

(IV)

(c) rearranging the compound of formula IV to produce the compound of formula V,

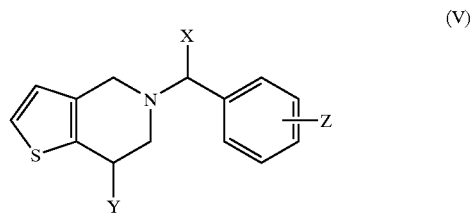

(V)

wherein Y is hydroxyl, alkanoyloxy, aroyloxy, carbamate or carbonate derivatives, and (d) reducing the compound of formula V to compound of formula I.

2. The process of claim 1 wherein Y is hydroxyl and the corresponding compound is α-(7-hydroxy-4,5,6,7-tetrahydrothieno[3,2-c]pyridyl)phenylacetic acid derivative of general formula

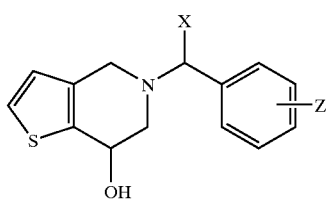

where X and Z have the same meaning as in claim 1.

3. The process of claim 1 wherein the compound of formula II is obtained through the reaction of primary amine of general formula

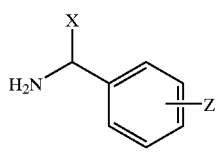

with an α substituted 2-acetylthiophene derivatives of general formula

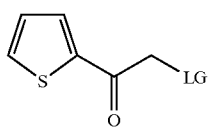

where X and Z have the same meaning as in claim 1 and LG is a leaving group selected from the group consisting of halogen, arylsulphonyloxy, alkylsulphonyloxy, and aroyloxy, in an aromatic solvent, polar aprotic solvent, polar protic solvent or mixtures thereof.

4. The process of claim 1 wherein the reduction of formula V to formula I in step (d) is obtained by direct dehydroxylation.

5. The process of claim 1 wherein the product of formula I in step (d) is obtained by derivatization of the hydroxyl group to a leaving group followed by reduction or stepwise elimination/reduction reaction sequence.

6. The process of claim 4 wherein the dehydroxylation is effected with stannous chloride under acidic conditions.

7. The process of claim 5 wherein the derivatization of hydroxyl group is effected with carbonyl diimidazole and heating, and wherein the reduction is effected by sodium borohydride.

8. The process of claim 1 wherein the compound of formula I is racemic or enantiomerically enriched clopidogrel or pharmaceutical salts thereof.

9. The process of claim 3 wherein the aromatic solvent is selected from the group consisting of toluene and equivalent thereof.

10. The process of claim 3 wherein the polar aprotic solvent is selected from dimethylformamide, hexamethylphosphoramide, ketones and combinations thereof.

11. The process of claim 3 wherein the polar protic solvents is selected from methanol, ethanol, propanol, n-propanol, butanol, n-butanol and combinations thereof.

12. A process for the preparation of clopidogrel comprising the steps of:

(a) reducing the compound of formula 20

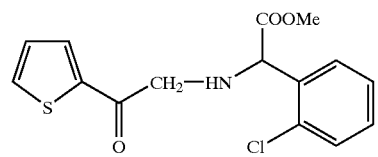

to give the compound of formula 21

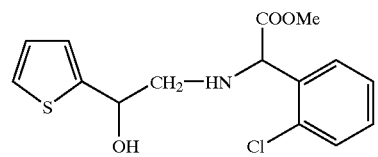

(b) reacting the compound of formula 21 with formaldehyde or with any chemical equivalent thereof to obtain the compound of formula 22

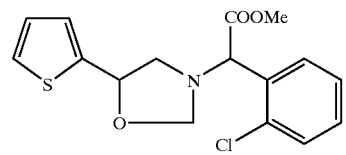

(c) rearranging the compound of formula 22 to obtain the compound of formula 23

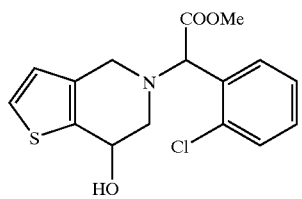

(d) and, reducing the compound of formula 23 to produce clopidogrel or pharmaceutically acceptable salt thereof.

13. The process of claim 12 wherein the compound of formula 20 is obtained by reacting the compound of formula 18

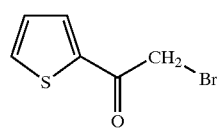

with the compound of formula 19

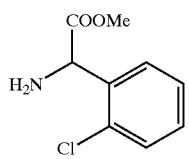

(19)

14. The process of claim 13 wherein the reaction of the compound of formula 18 with the compound of formula 19 is carried out in an aromatic solvent, polar aprotic solvent, polar protic solvent or mixtures thereof.

15. The process of claim 14 wherein the aromatic solvent is selected from the group consisting of toluene and equivalent thereof.

16. The process of claim 14 wherein the polar aprotic solvent is selected from the group consisting of dimethylformamide, hexamethylphosphoramide, ketones and combinations thereof.

17. The process of claim 14 wherein the polar protic solvents is selected from the group consisting of methanol, ethanol, propanol, n-propanol, butanol, n-butanol and combinations thereof.

18. A process for the preparation of methyl N-(2-(2-thienyl)-2-oxoethyl)-2-o-chlorophenylglycinate comprising the reaction of methyl 2-(o-chlorophenyl)glycine with 2-bromoacetylthiophene.

19. The process of claim 18 wherein the reaction is carried out in the presence of a base as an acid scavenger.

20. A process for the preparation of methyl N-(2-(2-thienyl)-2-hydroxyethyl)-2-o-chlorophenylglycinate comprising the reaction of methyl N-(2-(2-thienyl)-2-oxoethyl)-2-o-chlorophenylglycinate with a suitable reducing agent.

21. The process of claim 20 wherein the reducing agent is sodium borohydride.

22. A process for the preparation of 5-(2-thienyl)-3-(1-methoxycarbonyl-o-chlorobenzyl)-1,3-oxazoline comprising the reaction of methyl N-(2-(2-thienyl)-2-hydroxyethyl) 2-o-chlorophenylglycinate with formaldehyde.

23. 5-(2-thienyl)-3-(methoxycarbonyl-o-chlorobenzyl)-1, 3-oxazoline compound of formula

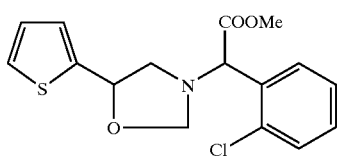

and its stereoisomers and pharmaceutically acceptable salts thereof.

24. A compound selected from the group consisting of 5R-(2-thienyl)-3-(1R-methoxycarbonyl-o-chlorobenzyl)-1, 3-oxazoline, 5R-(2-thienyl)-3-(1S-methoxycarbonyl-o-chlorobenzyl)-1,3-oxazoline, 5S-(2-thienyl)-3-(1R-methoxycarbonyl-o-chlorobenzyl)-1,3-oxazoline, and 5S-(2-thienyl)-3-(1S-methoxycarbonyl-o-chlorobenzyl)-1, 3oxazoline.

25. Methyl N-(2-(2-thienyl)-2-hydroxyethyl)-o-chlorophenylglycinate compound of formula

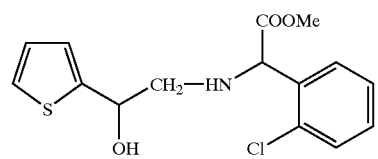

and its stereoisomers and pharmaceutically acceptable salts thereof.

26. A compound selected from the group consisting of Methyl N-(2R-(2-thienyl)-2-hydroxyethyl)-2R-o-chlorophenylglycinate, Methyl N-(2R-(2-thienyl)-2-hydroxyethyl)-2S-o-chlorophenylglycinate, Methyl N-(2S-(2-thienyl)-2-hydroxyethyl)-2R-o-chlorophenylglycinate, and Methyl N-(2S-(2-thienyl)-2-hydroxyethyl)-2S-o-chlorophenylglycinate.

27. Methyl N-(2-(2-thienyl)-2-oxoethyl)-2-chlorophenylglycinate of formula

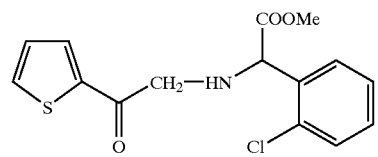

and its enantiomers and pharmaceutically acceptable salts thereof.

28. A compound selected from the group consisting of Methyl N-(2-(2-thienyl)-2-oxoethyl)-2R-o-chlorophenylglycinate and Methyl N-(2-(2-thienyl)-2-oxoethyl)-2S-o-chlorophenylglycinate.

* * * * *

UNITED STATES PATENT AND TRADEMARK OFFICE
CERTIFICATE OF CORRECTION

PATENT NO.    : 6,495,691 B1
DATED         : December 17, 2002
INVENTOR(S)   : Horne et al.

It is certified that error appears in the above-identified patent and that said Letters Patent is hereby corrected as shown below:

<u>Title page,</u>
Insert item: -- [30] Foreign Application Priority Data
            July 6, 2001 [CA] Canada....................2,352,520 --

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,495,691 B1
DATED         : December 17, 2002
INVENTOR(S)   : Stephen E. Horne et al.

Page 1 of 1

It is certified that error appears in the above-identified patent and that said Letters Patent is hereby corrected as shown below:

<u>Column 7,</u>
Line 30, after "I" and before "V", the word "and" should be changed to -- to --.

Signed and Sealed this

Fourth Day of May, 2004

JON W. DUDAS
*Acting Director of the United States Patent and Trademark Office*